Dec. 26, 1961 W. FLEMER III Plant Pat. 2,116
MAPLE TREE
Filed Feb. 23, 1961
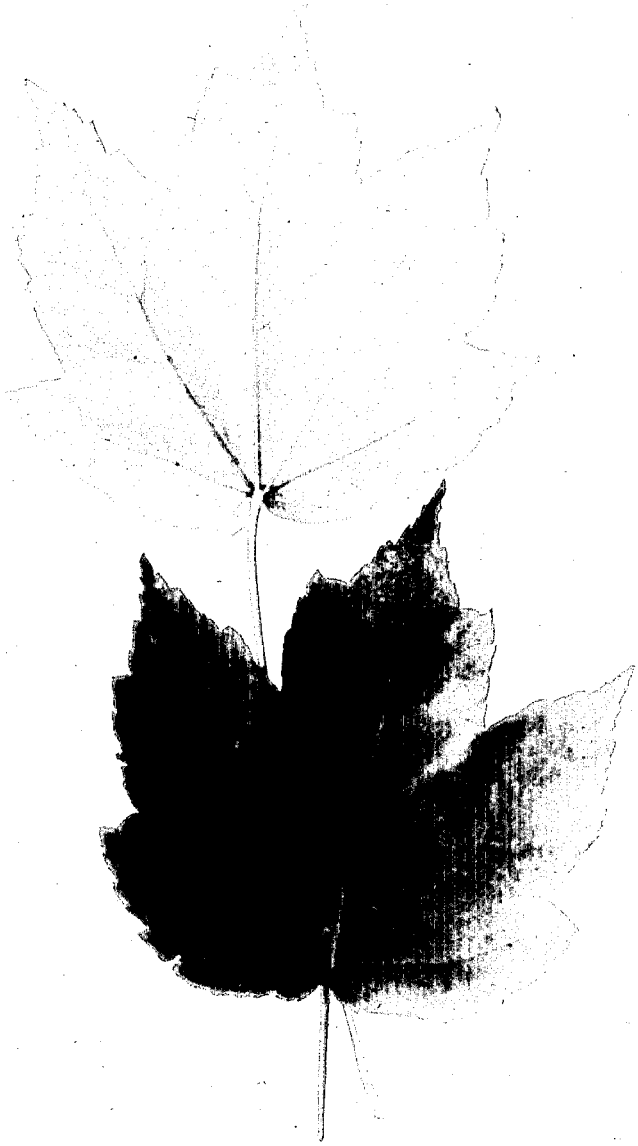
Inventor
William Flemer, III
By: Robb & Robb
Attorneys United States Patent Office Plant Pat. 2,116
Patented Dec. 26, 1961

2,116
MAPLE TREE

William Flemer III, Princeton, N.J., assignor to Princeton Nurserymen's Research Associates, Princeton, N.J., a partnership Filed Feb. 23, 1961, Ser. No. 91,289
1 Claim. (Cl. 47—59)

The present invention relates to a new and distinct variety of maple tree, which originated as an open-pollinated seedling of an unpatented maple tree botanically known as "*Acer rubrum columnare*" (Arnold Arboretum Form).

At the time this new variety was discovered by me, it was growing in nursery rows of "*Acer rubrum columnare*" (Arnold Arboretum Form) seedlings under my direct supervision and control. My attention was attracted to a particular seedling tree because of the fact that it was in Brilliant Red full autumn color when all other trees in the block were completely defoliated. I thereupon took steps to transplant this seedling for further close study, as the result of which, I found that the unusual foliage retention and prolonged fall color was constant, usually varying from 3 to 4 weeks longer than all other red maples. Although the male parent of this new open-pollinated seedling is unkown to me, I am convinced that the new seedling represents a new and distinct variety by virtue of the following unique combination of outstanding characteristics which distinguish it from all other varieties of which I am aware:

(1) A moderate rate of growth;

(2) Shapely oval head which is formed and maintained without costly pruning or staking;

(3) A habit of retaining the foliage from 3 to 4 weeks after all other red maples have defoliated; and (4) A distinctive and attractive Bright Crimson Red general color tonality of the foliage which is invariably attained in the fall season regardless of soil conditions or exposure.

Asexual reproduction of my new variety by budding (sometimes called bud-grafting), as performed at Princeton, New Jersey, shows that the foregoing characteristics and distinctions come true to form and are established and transmitted through succeeding propagations.

The accompanying drawing shows typical specimens of the foliage as depicted in color as nearly true as it is reasonably possible to make the same in a color illustration of this character, one of the specimens showing the upper surface which is darker in color than the under surface as depicted in the other specimen.

The following is a detailed description of my new variety, with color terminology in accordance with Munsell Color Chart, except where general color terms of ordinary dictionary significance are obvious:

Parentage: An open-pollinated seedling of "*Acer rubrum columnare*" (Arnold Arboretum Form).

Propagation: Holds its distinguishing characteristics through succeeding propagations by budding.

Locality where grown and observed: Princeton, New Jersey.

Tree: Medium size; vigorous; upright; with dense ovate head; medium rate of growth; hardy; relatively unproductive of fruits; uncertain bearer.

*Trunk.*—Stocky; smooth.

*Branches.*—Medium thickness; smooth-barked; dense branching. Color (1-year wood)—Light Maroon Red, plate 5.0R 3/8, value=3, chrome=8.

*Lenticils.*—Moderately abundant; small.

Foliage:

*Leaves.*—Thick; tough; with 3 major lobes plus 2 minor lobes on side of leaf; major lobes taper pointed and of medium thickness. Upper surface—smooth. Under surface—glaucous; pubescent along veins. Margin—serrate; width between serrations—6 mm.; depth of serrations—1 mm. Color: upper surface—Bright Crimson Red, Plate 5.0R 4/14, value=4, Chrome=14; under surface—Glaucous Red-Purple, Plate 7.5RP 5/10, value=5, chrome=10. Petiole—from 7 to 9 centimeters long; slender.

Flowers:

*Blooming season.*—Mid-season, as compared with other varieties.

*Size.*—Large, monoecious.

*Color.*—Bright Red, Plate 5.0R 4/14.

Fruit: Not significant; from 4 to 6 per fasicle; glabrous; about 2.5 centimeters long.

Disease and insect resistance: Good resistance to aphids and no susceptibility to tar spot disease such as is prevalent in many other Red maples, as determined by comparison with other varieties grown under the same conditions at Princeton, New Jersey.

I claim:

A new and distinct variety of maple tree, substantially as herein shown and described, characterized particularly as to novelty by the unique combination of a moderate rate of growth, attainment and retention of a shapely oval head without pruning or staking, a habit of retaining the foliage from 3 to 4 weeks longer than most other red maples, and a distinctive and attractive Bright Crimson Red general color tonality of the foliage.

No references cited.